United States Patent [19]

Takaya et al.

[11] Patent Number: 4,499,088
[45] Date of Patent: Feb. 12, 1985

[54] CEPHEM COMPOUNDS

[75] Inventors: Takao Takaya, Kawanishi; Hisashi Takasugi, Osaka; Hideaki Yamanaka, Hirakata, all of Japan

[73] Assignee: Fujisawa Pharmaceutical Co., Ltd., Osaka, Japan

[21] Appl. No.: 455,573

[22] Filed: Jan. 4, 1983

[51] Int. Cl.³ .................. A61K 31/545; C07D 501/56
[52] U.S. Cl. ..................... 514/202; 544/22; 544/27; 514/205; 514/206
[58] Field of Search .................. 424/246; 544/27, 22

[56] References Cited

U.S. PATENT DOCUMENTS

| | | | |
|---|---|---|---|
| 4,093,803 | 6/1978 | Cook et al. | 424/246 |
| 4,263,291 | 4/1981 | Takaya et al. | 424/246 |
| 4,278,793 | 7/1981 | Durckheimer et al. | 544/27 |
| 4,282,220 | 8/1981 | Bormann et al. | 544/28 |

FOREIGN PATENT DOCUMENTS 55-133385 10/1980 Japan .

Primary Examiner—Paul M. Coughlan, Jr.
Attorney, Agent, or Firm—Oblon, Fisher, Spivak, McClelland & Maier

[57] ABSTRACT

This invention relates to novel cephem compounds, of antimicrobial activity, of the formula:

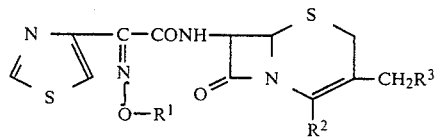

wherein
$R^1$ is carboxy $(C_1-C_6)$ alkyl or esterified carboxy $(C_1-C_6)$ alkyl,
$R^2$ is carboxy or an esterified carboxy group, and
$R^3$ is $(C_1-C_6)$ alkanoylamino, $(C_1-C_6)$ alkanesulfonyl, triazolylthio, tetrazolylthio having $(C_1-C_6)$ alkyl, pyridazinylthio having $(C_1-C_6)$ alkyl, thiadiazolylthio having $(C_1-C_6)$ alkyl, triazolopyridazinylthio or tetrazolopyridazinylthio, and pharmaceutically acceptable salts thereof.

10 Claims, No Drawings

CEPHEM COMPOUNDS

The present invention relates to new cephem compounds and pharmaceutically acceptable salts thereof. More particularly, it relates to new cephem compounds and pharmaceutically acceptable salts thereof, which have antimicrobial activities, to processes for preparation thereof, no pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms, especially for oral administration.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula:

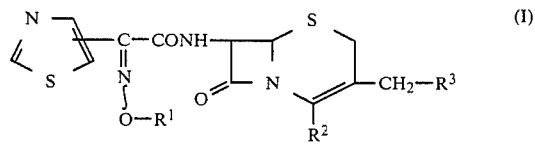

wherein
R¹ is carboxy(lower)alkyl or protected carboxy(lower)alkyl,
R² is carboxy or a protected carboxy group, and
R³ is a protected amino group, an acyl group, or a heterocyclicthio group which may have suitable substituent(s).

According to the present invention, the new cephem compounds (I) can be prepared by various processes which are illustrated in the following schemes.

Process 1

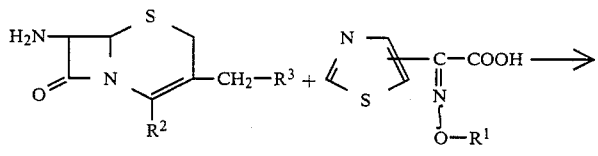

(II)  (III)

or its reactive derivatives at the amino group or a salt thereof or its reactive derivative at the carboxy group or a salt thereof

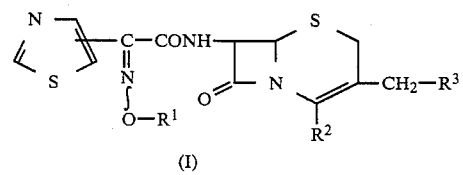

(I)

or a salt thereof

Process 2

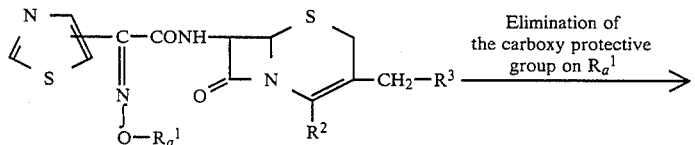

Elimination of the carboxy protective group on $R_a^1$ (Ia)

or a salt thereof

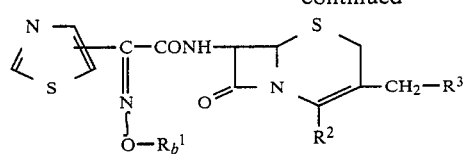

(Ib)

or a salt thereof

Process 3

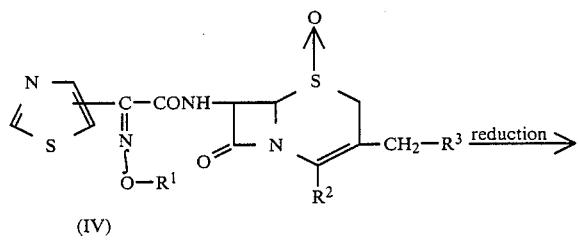

(IV)

or a salt thereof

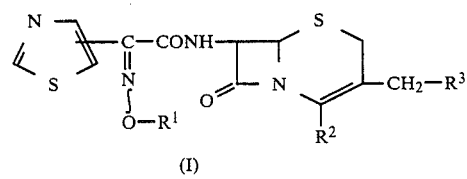

(I)

or a salt thereof

Process 4

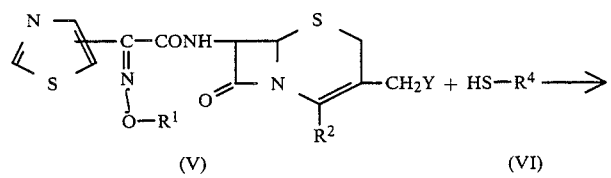

(V)     (VI)

or a salt thereof     or its reactive
derivative at the
mercapto group

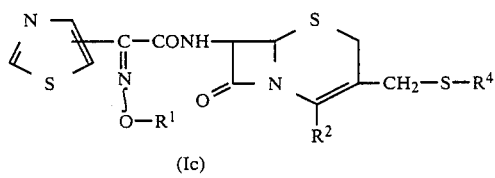

(Ic)

or a salt thereof wherein
  $R^1$, $R^2$ and $R^3$ are each as defined above,
  $R_a^1$ is protected carboxy(lower)alkyl,
  $R_b^1$ is carboxy(lower)alkyl,
  $R^4$ is a heterocyclic group which may have suitable substituent(s), and
  Y is a group which can be substituted by a group of the formula: —S—$R^4$ in which $R^4$ is as defined above.

The starting compound (V) and some of the starting compound (IV) are novel and can be prepared by the processes as illustrated by the following schemes.

Process A

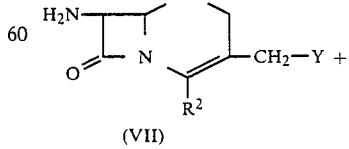

(VII)

or its reactive
derivative at the amino
group or a salt thereof

-continued

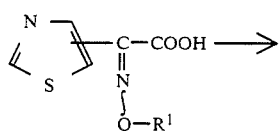

(III)

or its reactive derivative
at the carboxy group
or a salt thereof

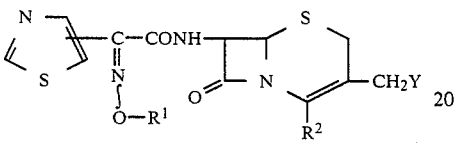

(V)

or a salt thereof

Process B

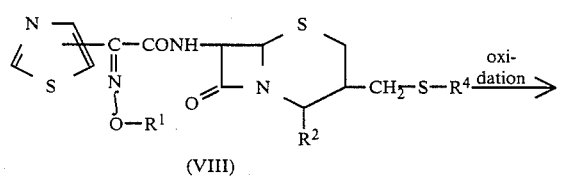

(VIII)

or a salt thereof

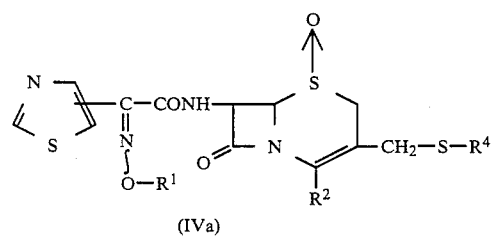

(IVa)

or a salt thereof

Process C

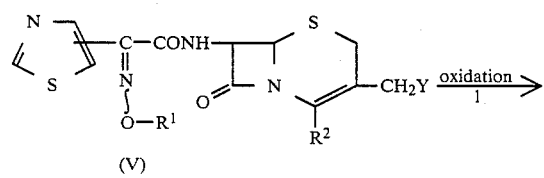

(V)

or a salt thereof

-continued

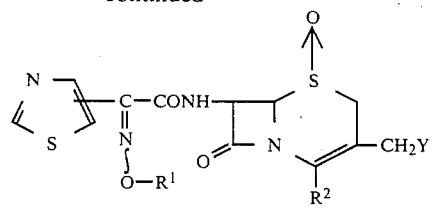

(IX)

or a salt thereof

HS—R⁴ (VI)
or its reactive
derivative at the
mercapto group

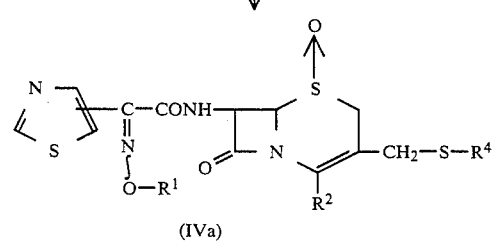

(IVa)

or a salt thereof

Process D

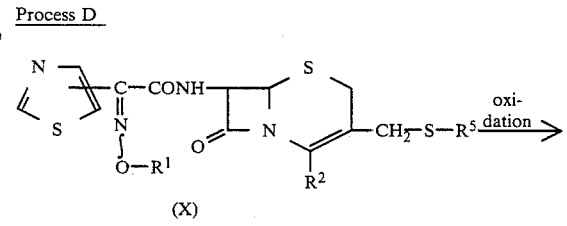

(X)

or a salt thereof

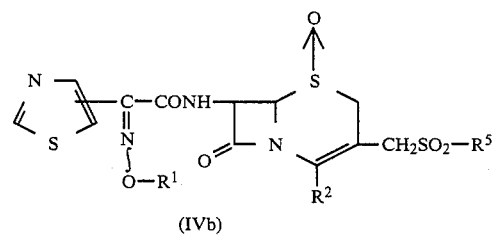

(IVb)

or a salt thereof wherein
R¹, R², R⁴ and Y are each as defined above, and
R⁵ is lower alkyl.

In the present invention, with regard to the compounds (I), (Ia), (Ib), (Ic), (III), (IV), (IVa), (IVb), (V), (VIII), (IX) and (X), it is to be understood that all of said compounds include syn isomer, anti isomer and a mixture thereof. And, as to the object compounds (I), the syn isomer thereof means one geometrical isomer having the group represented by the following formula:

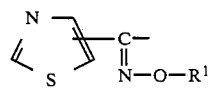

(wherein R¹ is as defined above)

and the anti isomer means the other geometrical isomer having the group of the formula:

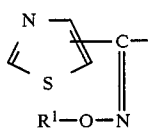

(wherein R¹ is as defined above)

Further, as to the other compounds, the syn and anti isomers thereof also are represented by the same geometrical configuration as that of the object compounds (I), respectively.

Suitable pharmaceutically acceptable salts of the object compounds (I) are conventional non-toxic salts and may include an inorganic salt, for example, a metal salt such as an alkali metal salt (e.g., sodium salt, potassium salt, etc.) and an alkaline earth metal salt (e.g., calcium salt, magnesium salt, etc.), ammonium salt etc.;

an organic salt, for example, an organic amine salt (e.g., trimethylamine salt, triethylamine salt, pyridine salt, procaine salt, picoline salt, dicyclohexylamine salt, N,N'-dibenzylethylene-diamine salt, N-methylglucamine salt, diethanolamine salt, triethanolamine salt, tris(hydroxymethylamino)methane salt, phenylethylbenzylamine salt, dibenzylethylenediamine salt, etc.) etc.;

an organic carboxylic or sulfonic acid salt (e.g., formate, acetate, maleate, tartrate, methanesulfonate, benzenesulfonate, toluenesulfonate, etc.); an inorganic acid salt (e.g., hydrochloride, hydrobromide, sulfate, phosphate, etc.);

a salt with a basic or acidic amino acid (e.g., arginine, aspartic acid, glutamic acid, lysine, etc.) and the like.

In the above and subsequent descriptions of the present specification, suitable examples and illustrations of the various definitions which the present invention include within the scope thereof are explained in detail as follows.

The term "lower" is intended to mean 1 to 6 carbon atoms, unless otherwise indicated.

Suitable "protected carboxy" and "protected carboxy moiety" in the term "protected carboxy(lower)alkyl" may include an esterified carboxy, and suitable examples of the ester moiety in said esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy-(lower)alkyl ester (e.g. acetoxymethyl ester, propionyloxymethyl ester, butyryloxymethyl ester, valeryloxymethyl ester, pivaloyloxymethyl ester, 2-acetoxyethyl ester, 2-propionyloxyethyl ester, hexanoyloxymethyl ester, etc.), lower alkanesulfonyl-(lower)alkyl ester (e.g. 2-mesylethyl ester, etc.) or mono(or di or tri)-halo(lower)alkyl ester (e.g. 2-iodoethyl ester, 2,2,2-trichloroethyl ester, etc.); lower alkenyl ester (e.g. vinyl ester, allyl ester, etc.);

lower alkynyl ester (e.g. etynyl ester, propynyl ester, etc.);

ar(lower)alkyl ester [e.g., mono(or di or tri)phenyl-(lower)alkyl ester, etc.] which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)-methyl ester, 3,4-dimethoxybenzyl ester, 4-hydroxy-3,5-di-tert-butylbenzyl ester, etc.);

aryl ester which may have at least one suitable substituent(s) (e.g. phenyl ester, 4-chlorophenyl ester, tolyl ester, tert-butylphenyl ester, xylyl ester, mesityl ester, cumenyl ester, etc.).

Suitable "lower alkyl" and "lower alkyl moiety" in the terms "carboxy(lower)alkyl" and "protected carboxy-(lower)alkyl" may include methyl, ethyl, propyl, isopropyl, butyl, t-butyl, pentyl, and hexyl.

Suitable "amino-protective group" in the term "a protected amino group" may include conventional one which is used in penicillin and cephalosporin compounds, for example, acyl as mentioned below, mono to triphenyl(lower)alkyl (e.g. benzyl, phenethyl, benzhydryl, trityl, etc.), lower alkoxycarbonyl(lower)alkylidene or its enamine tautomer (e.g. 1-methoxycarbonyl-1-propen-2-yl, etc.), di(lower)alkylaminomethylene (e.g. dimethylaminomethylene, etc.), etc.

Suitable acyl may include lower alkanoyl (e.g., formyl, acetyl, propionyl, butyryl, isobutyryl, valeryl, isovaleryl, oxalyl, succinyl, pivaloyl, etc.), preferably one having 1 to 4 carbon atom(s), more preferably one having 1 to 2 carbon atom(s); lower alkoxycarbonyl having 2 to 7 carbon atoms (e.g., methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.), preferably one having 3 to 6 carbon atoms;

lower alkanesulfonyl (e.g., mesyl, ethanesulfonyl, propanesulfonyl, isopropanesulfonyl, butanesulfonyl, etc.);

arenesulfonyl (e.g., benzenesulfonyl, tosyl, etc.); aroyl (e.g., benzoyl, toluoyl, naphthoyl, phthaloyl, indancarbonyl, etc.);

ar(lower)alkanoyl (e.g., phenylacetyl, phenylpropionyl, etc.); cyclo(lower)alkyl(lower)alkanoyl (e.g., cyclohexylacetyl, cyclopentylacetyl, etc.);

ar(lower)alkoxycarbonyl (e.g., benzyloxycarbonyl, phenethyloxycarbonyl, etc.).

Suitable "heterocyclic moiety" in the terms "a heterocyclicthio group which may have suitable substituent(s)" and "a heterocyclic group which may have suitable substituent(s)" means saturated or unsaturated, monocyclic or polycyclic heterocyclic group containing at least one hetero-atom such as an oxygen, sulfur, nitrogen atom and the like. And, especially preferably heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl, etc.; saturated 3 to 8-membered heteromonocyclic group containing 1 to 4 nitrogen atom(s), for example, pyrrolidinyl, imidazolidinyl, piperidino, piperazinyl, etc.;

unsaturated condensed heterocyclic group containing 1 to 5 nitrogen atom(s), for example, indolyl, isoindolyl, indolizynyl, benzimidazolyl, quinolyl, isoquinolyl, indazolyl, benzotriazolyl, tetrazolopyridyl, triazolopyridazinyl (e.g., 1,2,4-triazolo[4,3-b]pyridazinyl, etc.), dihydrotriazolopyridazinyl, tetrazolopyridazinyl (e.g., tetrazolo[1,5-b]pyridazinyl, etc.), etc.;

unsaturated 3- to 8-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.) etc.;

saturated 3 to 8-membered heteromonocyclic group containing 1 to 2 oxygen atom(s) and 1 to 3 nitrogen atom(s), for example, morpholinyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered heteromonocyclic group containing 1 to 2 sulfur atom(s) and 1 to 3 nitrogen atom(s), for example, thiazolyl, thiazolinyl, thiadiazolyl (e.g., 1,2,4-thiadiazolyl, 1,3,4-thiadiazolyl, 1,2,5-thiadiazolyl, etc.), etc.;

saturated 3 to 8-membered heteromonocyclic group containing 1 to 2 sulfur atom(s) and 1 to 3 nitrogen atom(s), for example, thiazolidinyl, etc.;

unsaturated 3 to 8-membered heteromonocyclic group containing a sulfur atom, for example, thienyl, etc.;

unsaturated condensed heterocyclic group containing 1 to 2 sulfur atom(s) and 1 to 3 nitrogen atom(s), for example, benzothiazolyl, benzothiadiazolyl, etc. and the like.

Suitable substituent(s) in the terms "a heterocyclicthio group which may have suitable substituent(s)" and "a heterocyclic group which may have suitable substituent(s)" may include lower alkyl (e.g., methyl, ethyl, propyl, isopropyl, butyl, isobutyl, t-butyl, pentyl, hexyl, etc.), and the like.

Suitable example of Y may include an acid residue such as azido, halogen (e.g., chlorine, bromine, fluorine or iodine) or acyloxy wherein acyl moiety is as mentioned above; and the like.

Preferable embodiments of the object compounds (I) are as follows.

Preferable embodiment of $R^1$ is carboxy(lower)alkyl or esterified carboxy(lower)alkyl [more preferably lower alkoxycarbonyl(lower)alkyl];

$R^2$ is carboxy or esterified carboxy [more preferably mono(or di or tri)phenyl(lower)alkoxycarbonyl];

$R^3$ is acylamino (more preferably lower alkanoylamino), an acyl group (more preferably lower alkanesulfonyl), unsaturated 3 to 8-membered heteromonocyclicthio containing 1 to 4 nitrogen atom(s) which may have lower alkyl (more preferably triazolylthio, tetrazolylthio having lower alkyl, or pyridazinylthio having lower alkyl), unsaturated 3 to 8-membered heteromonocyclicthio containing 1 to 2 sulfur atom(s) and 1 to 3 nitrogen atom(s) which has lower alkyl (more preferably thiadiazolylthio having lower alkyl), or unsaturated condensed heterocyclicthio containing 1 to 5 nitrogen atom(s) [more preferably triazolopyridazinylthio or tetrazolopyridazinylthio].

The processes for preparing the object compounds of the present invention are explained in details in the following.

PROCESS 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, trimethylsilylacetamide, bis(trimethylsilyl)urea or the like; a derivative formed by reaction of the compound (II) with phosphorus trichloride or phosgene, and the like. Suitable salts of the compound (II) can be referred to the ones as exemplified for compound (I). Suitable salts of the compound (III) may include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [$(CH_3)_2N^+=CH-$]ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine;

ethoxyacetylene; 1-alkoxy-1-chloroethylene; trialkyl phosphite; ethyl polyphosphate; isopropyl polyphosphate;

phosphorus oxychloride (phosphoryl chloride);

phosphorus trichloride; thionyl chloride; oxalyl chloride;

triphenylphosphine; 2-ethyl-7-hydroxybenzisoxazolium salt;

2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal carbonate, an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

PROCESS 2

The object compound (I$b$) or a salt thereof can be prepared by subjecting the compound (I$a$) or a salt thereof to elimination reaction of the carboxy protective group on R$_a^1$.

Suitable salts of the compounds (I$a$) and (I$b$) can be referred to the ones as exemplified for the compound (I).

The present reaction is carried out in accordance with a conventional method such as hydrolysis, reduction or the like.

In case that the protective group is an ester, the protective group can be eliminated by hydrolysis. Hydrolysis is preferably carried out in the presence of a base or an acid. Suitable base may include an inorganic base and an organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), picoline, 1,5-diazabicyclo[4,3,0]-none-5-ene, 1,4-diazabicyclo[2,2,2]octane, 1,8-diazabicyclo[5,4,0]undecene-7, or the like. Suitable acid may include an organic acid (e.g. formic acid, acetic acid, propionic acid, trifluoroacetic acid, etc.) and an inorganic acid (e.g. hydrochloric acid, hydrobromic acid, sulfuric acid, etc.). The acidic hydrolysis using trifluoroacetic acid is usually accelerated by addition of anisole.

The reaction is usually carried out in a solvent such as water, methylene chloride, an alcohol (e.g. methanol, ethanol, etc.), a mixture thereof or any other solvent which does not adversely influence the reaction. A liquid base or acid can be also used as the solvent. The reaction temperature is not critical and the reaction is usually carried out under cooling to warming.

Reduction can be applied preferably for elimination of the protective group such as 4-nitrobenzyl, 2-iodoethyl, 2,2,2-trichloroethyl, or the like. The reduction method applicable for the elimination reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst (e.g. palladium-carbon, etc.).

The present invention includes, within its scope, the case that the protected carboxy group in R$^2$ are converted into the free carboxy group during this reaction or the post-treating step of this reaction.

PROCESS 3

The compound (I) or a salt thereof can be prepared by reducing the compound (IV) or a salt thereof.

Suitable salts of the compound (IV) can be referred to the ones as exemplified for the compound (I).

The present reduction can be carried out by a conventional method which is applied to the transformation of

into —S—, for example, by using phosphorus trichloride, a combination of stannous chloride and acetyl chloride, a combination of an alkali metal iodide (e.g. sodium iodide, etc.) and trihaloacetic anhydride (e.g. trifluoroacetic anhydride, etc.), and the like.

The present reduction is usually carried out in a solvent such as acetone, dioxane, acetonitrile, benzene, hexane, chloroform, methylene chloride, ethylene chloride, tetrahydrofuran, ethyl acetate, N,N-dimethylformamide or any other solvents which do not adversely affect the reaction.

The reaction temperature is not critical and the reaction is usually carried out under cooling or at ambient temperature.

PROCESS 4

The compound (I$c$) or a salt thereof can be prepared by reacting the compound (V) or a salt thereof with the compound (VI) or its reactive derivative at the mercapto group.

Suitable salts of the compound (I$c$) can be referred to the ones as exemplified for the compound (I). Suitable salts of the compound (V) can be referred to the ones as exemplified for the compound (III).

Suitable reactive derivative at the mercapto group in the compound (VI) may include a metal salt such as an alkali metal salt (e.g. sodium salt, potassium salt, etc.), an alkaline earth metal salt (e.g., magnesium salt, etc.) or the like.

The reaction is usually carried out in a solvent such as water, acetone, chloroform, nitrobenzene, methylene chloride, ethylene chloride, N,N-dimethylformamide, methanol, ethanol, ether, tetrahydrofuran or any other conventional solvents which do not adversely influence the reaction, preferably in ones having strong polarity, which may be used as a mixture with water.

When the compound (V) and/or the compound (VI) are used in free form in the reactions, the reaction is preferably carried out in the presence of a base such as alkali metal hydroxide, alkali metal carbonate, alkali metal bicarbonate, trialkylamine, pyridine, or a Lewis acid such as boron trifluoride or the like, and preferably carried out around neutral conditions. The reaction temperature is not critical and the reaction is usually carried out under cooling, at ambient temperature or under warming.

The processes for preparing the starting compound (V) and some of the starting compound (IV) of the present invention are explained in detail of the following.

PROCESS A

The compound (V) or a salt thereof can be prepared by reacting the compound (VII) or its reactive derivative at the amino group or a salt thereof with the compound (III) or its reactive derivative at the carboxy group or a salt thereof.

Suitable salts of the compound (VII) can be referred to the ones as exemplified for compound (I).

Suitable reactive derivative at the amino group of the compound (VII) can be referred to the ones as exemplified for compound (II).

The present reaction can be carried out in a similar manner to that of aforementioned Process 1.

PROCESS B

The compound (IVa) or a salt thereof can be prepared by oxidizing the compound (VIII) or a salt thereof.

Suitable salts of the compounds (IVa) and (VIII) can be referred to the ones as exemplified for the compound (I).

The present oxidation reaction can be carried out by a conventional method which is applied for the transformation of —S— into

for example by using an oxidizing agent such as m-chloroperbenzoic acid, perbenzoic acid, peracetic acid, ozone, hydrogen peroxide, periodic acid or the like.

The present reaction is usually carried out in a solvent such as water, acetone, dioxane, acetonitril, chloroform, methylene chloride, tetrahydrofuran, acetic acid, ethyl acetate or any other solvents which do not adversely affect the reaction.

The present reaction can also be carried out in the presence of a catalyst such as an alkali metal tungstate (e.g., sodium tungstate, potassium tungstate, etc.) or the like.

The reaction temperature is not critical and the reaction is preferably carried out under cooling or at ambient temperature.

PROCESS C-(1)

The compound (IX) or a salt thereof can be prepared by oxidizing the compound (V) or a salt thereof.

Suitable salts of the compound (IX) can be referred to the ones as exemplified for compound (III).

The present reaction can be carried out in a similar manner to that of aforementioned Process B.

PROCESS C-(2)

The compound (IVa) or a salt thereof can be prepared by reacting the compound (IX) or a salt thereof with the compound (VI) or its reactive derivative at the mercepto group.

The present reaction can be carried out in a similar manner to that of aforementioned Process 4.

PROCESS D

The compound (IVb) or a salt thereof can be prepared by oxidizing the compound (X) or a salt thereof. Suitable salts of the compounds (IVb) and (X) can be referred to the ones as exemplified for compound (III).

The present reaction can be carried out in a similar manner to that of aforementioned Process B.

The object compounds (I) and pharmaceutically acceptable salts thereof of the present invention are novel compounds which exhibit high antibacterial activity and inhibit the growth of a wide variety of pathogenic microorganisms including Gram-positive and Gram-negative bacteria and are useful as antimicrobial agents, especially for oral administration. For therapeutic purpose, the compounds according to the present invention can be used in the form of conventional pharmaceutical preparation which contain said compounds, as an active ingredient, in admixture with a pharmaceutically acceptable carrier such as an organic or an inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives, such as lactose, fumaric acid, citric acid, tartaric acid, stearic acid, maleic acid, succinic acid, malic acid, magnesium stearate, terra alba, sucrose, corn starch, talc, gelatin, agar, pectin, peanut oil, olive oil, cacao butter, ethylene glycol and the like.

While the dosage of the compounds will vary depending upon the age and condition of the patient, an average single dose of about 10 mg, 50 mg, 100 mg, 250 mg, 500 mg, and 1000 mg of the compounds according to the present invention was proved to be effective for treating infectious diseases caused by pathogenic bacteria. In general, amounts between 1 mg/body and about 6,000 mg/body or even more may be administered per day.

In order to illustrate the usefulness of the object compound, anti-microbial activities, urinary excretion and biliary excretion of a representative compound of the present invention are shown below.

[1] Test Compound:

7-[2-Carboxymethoxyimino-2-(4-thiazolyl)acetamido]-3-(tetrazolo[1,5-b]pyridazin-6-yl)thiomethyl-3-cephem-4-carboxylic acid (syn isomer).
(hereinafter referred to as Test Compound (1))

[2] Test:

(A) Minimal inhibitory concentration
(1) Test Method

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in terms of μg/ml after incubation at 37° C. for 20 hours.

(2) Test Results

| Test strains | MIC (μg/ml) Test Compound (1) |
|---|---|
| *Proteus mirabilis* 18 | <0.025 |
| *Proteus vulgaris* 2 | <0.025 |

(B) Urinary excretion (1) Test Method

Urine of rats was collected with a urine collector at 0 to 6, and 6 to 24 hours after oral administration of 100 mg/kg of the test antibiotic. The antibiotic levels in the urine samples were bioassayed with the standard solution prepared with M/15 phosphate buffer (pH 7.0) and the urinary recovery in 24 hours was calculated.

(2) Test Result

|  | Urinary recovery in 24 hours (%) |
|---|---|
| Test Compound (1) | 20.22 |

(C) Biliary excretion (1) Test Method

Rats anesthetized with pentobarbital were fixed in supine position, and a polyethylene cannula was inserted into the bile duct. Bile samples were collected at 0 to 3, 3 to 6, and 6 to 24 hours after oral administration of 100 mg/kg of the test antibiotic. The antibiotic levels in the bile samples were bioassayed with the standard solutions prepared with M/15 phosphate buffer (pH 7.0) and the biliary recovery in 24 hours were calculated.

(2) Test Result

|  | Biliary recovery in 24 hours (%) |
|---|---|
| Test Compound (1) | 8.97 |

The following preparations and examples are given for the purpose of illustrating the present invention in more detail.

Preparation 1

A mixture of 2-t-butoxycarbonylmethoxyimino-2-(2-formamidothiazol-4-yl)acetic acid (syn isomer) (15.0 g) and conc. hydrochloric acid (9.5 g) in methanol (75 ml) was stirred at ambient temperature for 2.5 hours. Water (100 ml) was added to the reaction mixture and the solution was adjusted to pH 3.0 with 10% aqueous solution of sodium hydroxide under stirring. The precipitates were collected by filtration, washed with water and diisopropyl ether and dried to give 2-t-butoxycarbonylmethoxyimino-2-(2-aminothiazol-4-yl)acetic acid (syn isomer) (12.7 g).

IR (Nujol): 3340, 1740, 1630 cm$^{-1}$.

NMR (DMSO-$d_6$, δ): 1.43 (9H, s), 4.51 (2H, s), 6.77 (3H, s).

Preparation 2

To a suspension of 2-t-butoxycarbonylmethoxyimino-2-(2-aminothiazol-4-yl)acetic acid (syn isomer) (11.5 g) in tetrahydrofuran (80.5 ml) was added dropwise a solution of t-butyl nitrite (6.5 g) in tetrahydrofuran (32.5 ml) at 50° to 57° C. under stirring, and the mixture was stirred at 50° to 55° C. for 20 minutes.

The reaction mixture was poured into a mixture of ethyl acetate and water and the solution was acidified to pH 1.0 with 10% hydrochloric acid.

Water (60 ml) was added to the separated organic layer and the mixture was adjusted to pH 6.0 with 40% aqueous solution of potassium carbonate. The separated aqueous solution was washed with ethyl acetate and the solution was acidified to pH 2.8 with 10% hydrochloric acid. The acidified solution was extracted with ethyl acetate and the ethyl acetate layer was dried over magnesium sulfate and evaporated. The residue was triturated with diisopropyl ether to give 2-t-butoxycarbonylmethoxyimino-2-(4-thiazolyl)acetic acid (syn isomer) (6.1 g), mp. 141° C. (dec.).

IR (Nujol): 1730 cm$^{-1}$.

NMR (DMSO-$d_6$, δ): 1.46 (9H, s), 4.69 (2H, s), 8.08 (1H, d, J=2.0 Hz), 9.21 (1H, d, J=2.0 Hz).

Preparation 3

Vilsmeier reagent was prepared from phosphorus oxychloride (14.4 g) and N,N-dimethylformamide (6.9 g) in ethyl acetate (27.6 ml) in a usual manner. 2-t-Butoxycarbonylmethoxyimino-2-(4-thiazolyl)acetic acid (syn isomer) (22.8 g) was added to the stirred suspension of Vilsmeier reagent in ethyl acetate (200 ml) under ice-cooling and the mixture was stirred for 20 minutes at the same temperature to produce an activated acid solution. Trimethylsilylacetamide (56.9 g) was added to a stirred suspension of benzhydryl 7-amino-3-chloromethyl-3-cephem-4-carboxylate (30 g) in ethyl acetate (300 ml) and the resultant mixture was stirred for 30 minutes at ambient temperature. To the solution was added the activated acid solution obtained above at $-10°$ C. and the mixture was stirred for 30 minutes at the same temperature. Water was added to the reaction mixture, and the separated organic layer was washed with a saturated aqueous solution of sodium bicarbonate and a saturated aqueous solution of sodium chloride, successively. The ethyl acetate layer was dried over magnesium sulfate and evaporated to give benzhydryl 7-[2-t-butoxycarbonylmethoxyimino-2-(4-thiazolyl)acetamido]-3-chloromethyl-3-cephem-4-carboxylate (syn isomer) (37.3 g).

IR (Nujol): 1775, 1730, 1680 cm$^{-1}$.

NMR(DMSO-$d_6$, δ): 1.45 (9H, s), 3.69 (2H, m), 4.48 (2H, s), 4.68 (2H, s), 5.33 (1H, d, J=5.0 Hz), 6.03 (1H, d, J=5.0 Hz, 8.0 Hz), 7.02 (1H, s), 7.20–7.73 (10H, m), 7.98 (1H, d, J=2.0 Hz), 9.22 (1H, d, J=2.0 Hz), 9.70 (1H, d, J=8.0 Hz).

Preparation 4

The following compound was obtained according to a similar manner to that of Preparation 3.

Benzhydryl 7-[2-t-butoxycarbonylmethoxyimino-2-(4-thiazolyl)acetamido]-3-methylthiomethyl-3-cephem-4-carboxylate (syn isomer).

IR (Nujol): 3270, 1770, 1720, 1660 cm$^{-1}$.

NMR (DMSO-$d_6$, δ): 1.42 (9H, s), 1.78 (3H, s), 3.42–3.73 (4H, m), 4.61 (2H, s), 5.26 (1H, d, J=4.0 Hz), 5.87 (1H, dd, J=4.0 Hz, 8.0 Hz), 6.88 (1H, s), 7.13–7.60 (10H, m), 7.91 (1H, d, J=2.0 Hz), 9.11 (1H, d, J=2.0 Hz), 9.56 (1H, d, J=8.0 Hz).

Preparation 5

A solution of m-chloroperbenzoic acid (0.4 g) (purity: 80%) in ethyl acetate (5 ml) was added to a solution of a mixture (1.4 g) of benzhydryl 7-[2-t-butoxycarbonylmethoxyimino-2-(4-thiazolyl)acetamido]-3-(1,2,4-triazolo[4,3-b]pyridazin-6-yl)thiomethyl-3-cephem-4-carboxylate (syn isomer) and benzhydryl 7-[2-t-butoxycarbonylmethoxyimino-2-(4-thiazolyl)acetamido]-3-(1,2,4-triazolo[4,3-b]pyridazin-6-yl)thiomethyl-2-cephem-4-carboxylate (syn isomer) in ethyl acetate (10 ml) under ice-cooling and the resultant mixture was stirred for 1 hour at the same temperature. The resulting solution was washed with a saturated aqueous solution of sodium bicarbonate and a saturated aqueous solution of sodium chloride, successively. The organic layer was dried over magnesium sulfate and evaporated to give benzhydryl 7-[2-t-butoxycarbonylmethoxyimino-2-(4-thiazolyl)acetamido]-3-(1,2,4-triazolo[4,3-b]pyridazin-6-yl)thiomethyl-3-cephem-4-carboxylate-1-oxide (syn isomer) (1.3 g).

IR (Nujol): 1790, 1775, 1720 cm$^{-1}$.

NMR (DMSO-$d_6$, δ): 1.44 (9H, s), 4.50–4.81 (4H, m), 3.98 (2H, s), 5.04 (1H, d, J=5.0 Hz), 6.07 (1H, d, J=5.0 Hz, 8.0 Hz), 7.05–7.68 (11H, m), 8.00 (1H, d, J=2.0 Hz), 8.14 (1H, d, J=10.0 Hz), 8.77 (1H, d, J=8.0 Hz), 9.07–9.23 (2H, m).

Preparation 6

The following compound was obtained by reacting benzhydryl 7-[2-t-butoxycarbonylmethoxyimino-2-(4-thiazolyl)acetamido]-3-chloromethyl-3-cephem-4-carboxylate (syn isomer) with m-chloroperbenzoic acid according to a similar manner to that of Preparation 5.

Benzhydryl 7-[2-t-butoxycarbonylmethoxyimino-2-(4-thiazolyl)acetamido]-3-chloromethyl-3-cephem-4-carboxylate-1-oxide (syn isomer).

IR (Nujol): 1785, 1720, 1670 cm$^{-1}$.

NMR (DMSO-$d_6$, δ): 1.46 (9H, s), 3.93 (2H, m), 4.61 (2H, m), 4.71 (2H, s), 5.18 (1H, d, J=5.0 Hz), 6.18 (1H, d, J=5.0 Hz, 8.0 Hz), 7.04 (1H, s), 7.24–7.73 (10H, s), 8.06 (1H, d, J=2.0 Hz), 8.90 (1H, d, J=8.0 Hz), 9.22 (1H, d, J=2.0 Hz).

Preparation 7

3-Mercapto-6-methylpyridazine (1 g) was added to a mixture of benzhydryl 7-[2-t-butoxycarbonylmethoxyimino-2-(4-thiazolyl)acetamido]-3-chloromethyl-3-cephem-4-carboxylate-1-oxide (syn isomer) (5.0 g) in N,N-dimethylformamide (25 ml) and triethylamine (0.7 g) under ice-cooling and the mixture was stirred for 3 hours at the same temperature. The reaction mixture was added to a mixture of ethyl acetate and water. The separated organic layer was washed with a saturated aqueous solution of sodium chloride, dried over magnesium sulfate and evaporated to give benzhydryl 7-[2-t-butoxycarbonylmethoxyimino-2-(4-thiazolyl)acetamido]-3-(6-methylpyridazin-3-yl)thiomethyl-3-cephem-4-carboxylate-1-oxide (syn isomer) (4.8 g).

IR (Nujol): 1780, 1715, 1665 cm$^{-1}$.

NMR (DMSO-$d_6$, δ): 2.30 (3H, s), 4.03 (2H, m), 4.72 (4H, m), 5.14 (1H, d, J=4.0 Hz), 6.15 (1H, dd, J=4.0 Hz, 8.0 Hz), 7.04 (1H, s), 7.08–7.78 (12H, m), 8.06 (1H, d, J=2.0 Hz), 8.83 (1H, d, J=8.0 Hz), 9.21 (1H, d, J=2.0 Hz).

Preparation 8

The following compound was obtained according to a similar manner to that of Preparation 7.

Benzhydryl 7-[2-t-butoxycarbonylmethoxyimino-2-(4-thiazolyl)acetamido]-3-(1,2,4-triazolo[4,3-b]pyridazin-6-yl)thiomethyl-3-cephem-4-carboxylate-1-oxide (syn isomer).

IR (Nujol): 1790, 1775, 1720 cm$^{-1}$.

Preparation 9

A mixture of 7-[2-t-butoxycarbonylmethoxyimino)-2-(4-thiazolyl)acetamido]-3-methylthiomethyl-3-cephem-4-carboxylic acid (syn isomer) (2.64 g), methylene chloride (50 ml) and acetic acid (50 ml) was stirred for 10 minutes at ambient temperature to give a clear solution. To the solution were added sodium tungstate (0.1 g) and 30% aqueous solution (1.7 g) of hydrogen peroxide in water (8 ml) and the resultant mixture was stirred for 1 hour at ambient temperature. The reaction mixture was filtered off, washed with methylene chloride, and the filtrate and washings were evaporated. The oily residue was added to diisopropyl ether (700 ml).

The resultant precipitate was collected by filtration, washed with diisopropyl ether and dried to give 7-[2-t-butoxycarbonylmethoxyimino-2-(4-thiazolyl)acetamido]-3-mesylmethyl-3-cephem-4-carboxylic acid-1-oxide (syn isomer).

IR (Nujol): 3280, 1770, 1720, 1680, 1540 cm$^{-1}$.

NMR (DMSO-$d_6$, δ): 1.43 (9H, s), 3.0 (3H, s), 3.95 (2H, ABq, J=18 Hz), 4.50 (2H, ABq, J=13 Hz), 4.67 (2H, s), 5.15 (1H, d, J=5 Hz), 6.02 (1H, dd, J=5 Hz, 8 Hz), 8.03 (1H, d, J=2 Hz), 8.80 (1H, d, J=8 Hz), 9.18 (1H, d, J=2 Hz).

EXAMPLE 1

Vilsmeier reagent was prepared from phosphorus oxychloride (1.6 g) and N,N-dimethylformamide (0.8 g) in ethyl acetate (3.2 ml) in a usual manner. 2-t-Butoxycarbonylmethoxyimino-2-(4-thiazolyl)acetic acid (syn isomer) (2.5 g) was added to the stirred suspension of Vilsmeier reagent in ethyl acetate (20 ml) under ice-cooling and the resultant mixture was stirred for 20 minutes at the same temperature to produce an activated acid solution. 7-Amino-3-(tetrazolo[1,5-b]-pyridazin-6-yl)thiomethyl-3-cephem-4-carboxylic acid (3.5 g) was dissolved in a solution of sodium bicarbonate (2.4 g) in a mixture of water (26 ml) and acetone (26 ml). To the solution was added the activated acid solution obtained above at −3° to 3° C. and the solution was stirred for 30 minutes under keeping the pH 7 to 8 with 20% aqueous solution of sodium carbonate. Water and ethyl acetate were added to the reaction mixture and the mixture was adjusted to pH 2.0 with 10% hydrochloric acid. The separated organic layer was washed with saturated aqueous solution of sodium chloride, dried over magnesium sulfate and evaporated to give 7-[2-t-butoxycarbonylmethoxyimino-2-(4-thiazolyl)acetamido]-3-(tetrazolo[1,5-b]pyridazin-6-yl)thiomethyl-3-cephem-4-carboxylic acid (syn isomer) (3.7 g).

IR (Nujol): 1770, 1710, 1670 cm$^{-1}$.

NMR (DMSO-$d_6$, δ): 1.45 (9H, s), 3.76 (2H, m), 4.45 (2H, q, J=14.0 Hz), 4.66 (2H, s), 5.21 (1H, d, J=5.0 Hz), 5.87 (1H, dd, J=5.0 Hz, 8.0 Hz), 7.74 (1H, d, J=10.0 Hz), 7.95 (1H, d, J=2.0 Hz), 8.58 (1H, d, J=10.0 Hz), 9.15 (1H, d, J=2.0 Hz), 9.60 (1H, d, J=8.0 Hz).

EXAMPLE 2

Vilsmeier reagent was prepared from phosphorus oxychloride (1.9 g) and N,N-dimethylformamide (0.9 g) in ethyl acetate (3.6 ml) in a usual manner. 2-t-Butoxycarbonylmethoxyimino-2-(4-thiazolyl)acetic acid (syn isomer) (3.0 g) was added to the stirred suspension of Vilsmeier reagent in ethyl acetate (30 ml) under ice-cooling and the mixture was stirred for 20 minutes at the same temperature to produce an activated acid solution. Bis(trimethylsilyl)urea (5.8 g) was added to a stirred suspension of 7-amino-3-(1-methyl-1H-tetrazol-5-yl)thiomethyl-3-cephem-4-carboxylic acid (3.1 g) in tetrahydrofuran (30 ml) and the mixture was stirred for 20 minutes at 35° to 40° C. To the resultant solution was added the activated acid solution obtained above at −10° C. and the mixture was stirred for 30 minutes at the same temperature. Water and ethyl acetate were added to the reaction mixture and the separated organic layer was added to water, and the mixture was adjusted to pH 7.5 with 20% aqueous solution of potassium carbonate. The separated aqueous layer was adjusted to pH 2 with 10% hydrochloric acid and extracted with ethyl acetate. The extract layer was washed with saturated aqueous solution of sodium chloride, dried over magnesium sulfate and evaporated to give 7-[2-t-butoxycarbonylmethoxyimino-2-(4-thiazolyl)acetamido]-3-(1-methyl-1H-tetrazol-5-yl)-thiomethyl-3-cephem-4-carboxylic acid (syn isomer) (4.7 g).

IR (Nujol): 3260, 1760, 1720, 1680, 1630 cm$^{-1}$.

NMR (DMSO-d$_6$, δ): 1.45 (9H, s), 3.92 (2H, q, J=18.0 Hz), 3.96 (3H, s), 4.33 (2H, q, J=14.0 Hz), 4.66 (2H, s), 5.18 (1H, d, J=5.0 Hz), 5.87 (1H, dd, J=5.0 Hz, 8.0 Hz), 7.96 (1H, d, J=2.0 Hz), 9.19 (1H, d, J=2.0 Hz), 9.63 (1H, d, J=8.0 Hz).

EXAMPLE 3

The following compounds were obtained according to similar manners to those of Examples 1 and 2.

(1) 7-[2-Carboxymethoxyimino-2-(4-thiazolyl)acetamido]-3-(tetrazolo[1,5-b]pyridazin-6-yl)thiomethyl-3-cephem-4-carboxylic acid (syn isomer).

IR (Nujol): 3200, 1775, 1715, 1675 cm$^{-1}$.

(2) 7-[2-Carboxymethoxyimino-2-(4-thiazolyl)acetamido]-3-(1-methyl-1H-tetrazol-5-yl)thiomethyl-3-cephem-4-carboxylic acid. (syn isomer)

IR (Nujol): 1775, 1720, 1675 cm$^{-1}$.

(3) 7-[2-t-Butoxycarbonylmethoxyimino-2-(4-thiazolyl)acetamido]-3-(5-methyl-1,3,4,-thiadiazol-2-yl)-thiomethyl-3-cephem-4-carboxylic acid (syn isomer).

IR (Nujol): 1770, 1720, 1670 cm$^{-1}$.

NMR (DMSO-d$_6$, δ): 1.45 (9H, s), 2.69 (3H, s), 3.71 (2H, q, J=18.0 Hz), 4.40 (2H, q, J=14.0 Hz), 4.67 (2H, s), 5.21 (1H, d, J=4.0 Hz), 5.87 (1H, dd, J=4.0 Hz, 8.0 Hz), 7.97 (1H, d, J=2.0 Hz), 9.20 (1H, d, J=2.0 Hz), 9.62 (1H, d, J=4.0 Hz).

(4) 7-[2-Carboxymethoxyimino-2-(4-thiazolyl)acetamido]-3-(5-methyl-1,3,4-thiadiazol-2-yl)thiomethyl-3-cephem-4-carboxylic acid (syn isomer)

IR (Nujol): 1775, 1720, 1675 cm$^{-1}$.

(5) 7-[2-t-Butoxycarbonylmethoxyimino-2-(4-thiazolyl)-acetamido]-3-(1H-1,2,3-triazol-5-yl)thiomethyl-3-cephem-4-carboxylic acid (syn isomer).

IR (Nujol): 1770, 1710, 1670 cm$^{-1}$.

NMR (DMSO-d$_6$, δ): 1.45 (9H, s), 3.67 (2H, q, J=18.0 Hz), 3.97 (2H, q, J=14.0 Hz), 4.66 (2H, s), 5.19 (1H, d, J=5.0 Hz), 5.84 (1H, dd, J=5.0 Hz, 8.0 Hz), 7.95 (3H, m), 9.19 (1H, d, J=2.0 Hz), 9.61 (1H, d, J=8.0 Hz).

(6) 7-[2-Carboxymethoxyimino-2-(4-thiazolyl)acetamido]-3-(1H-1,2,3-triazol-5-yl)thiomethyl-3-cephem-4-carboxylic acid (syn isomer).

IR (Nujol): 1775, 1720, 1675 cm$^{-1}$.

(7) 7-[2-t-Butoxycarbonylmethoxyimino-2-(4-thiazolyl)-acetamido]-3-acetamidomethyl-3-cephem-4-carboxylic acid (syn isomer).

IR (Nujol): 3250, 1780, 1710, 1680, 1600, 1550 cm$^{-1}$.

NMR (DMSO-d$_6$, δ): 1.43 (9H, s), 1.53 (3H, s), 3.48 (2H, ABq, J=18 Hz), 4.10 (2H, q, J=13 Hz), 4.67 (2H, s), 5.17 (1H, d, J=5 Hz), 5.83 (1H, dd, J=5 Hz, 8 Hz), 8.0 (1H, d, J=2 Hz), 9.23 (1H, d, J=2 Hz), 9.58 (1H, d, J=8 Hz).

(8) 7-[2-Carboxymethoxyimino-2-(4-thiazolyl)acetamido]-3-acetamidomethyl-3-cephem-4-carboxylic acid (syn isomer).

IR (Nujol): 3250, 1775, 1720, 1670, 1540 cm$^{-1}$.

(9) Benzhydryl 7-[2-t-butoxycarbonylmethoxyimino-2-(4-thiazolyl)acetamido]-3-(6-methylpyridazin-3-yl)-thiomethyl-3-cephem-4-carboxylate (syn isomer).

IR (Nujol): 1780, 1720, 1675, 1630 cm$^{-1}$.

(10) 7-[2-Carboxymethoxyimino-2-(4-thiazolyl)acetamido]-3-(6-methylpyridazin-3-yl)thiomethyl-3-cephem-4-carboxylic acid (syn isomer).

IR (Nujol): 1770, 1675 cm$^{-1}$.

(11) 7-[2-t-Butoxycarbonylmethoxyimino-2-(4-thiazolyl)-acetamido]-3-mesylmethyl-3-cephem-4-carboxylic acid (syn isomer)

IR (Nujol): 3250, 1770, 1710, 1650, 1550 cm$^{-1}$.

(12) 7-[2-Carboxymethoxyimino-2-(4-thiazolyl)acetamido]-3-mesylmethyl-3-cephem-4-carboxylic acid (syn isomer).

IR (Nujol): 3250, 1780, 1720, 1675, 1540 cm$^{-1}$.

(13) Benzhydryl 7-[2-t-butoxycarbonylmethoxyimino-2-(4-thiazolyl)acetamido]-3-(1,2,4-triazolo[4,3-b]pyridazin-6-yl)thiomethyl-3-cephem-4-carboxylate (syn isomer).

IR (Nujol): 1775, 1715, 1675 cm$^{-1}$.

(14) 7-[2-Carboxymethoxyimino-2-(4-thiazolyl)acetamido]-3-(1,2,4-triazolo[4,3-b]pyridazin-6-yl)thiomethyl-3-cephem-4-carboxylic acid (syn isomer).

IR (Nujol): 1770, 1680 cm$^{-1}$.

EXAMPLE 4

Trifluoroacetic acid (14.4 ml) was added to a suspension of 7-[2-t-butoxycarbonylmethoxyimino-2-(4-thiazolyl)acetamido]-3-(tetrazolo[1,5-b]pyridazin-6-yl)-thiomethyl-3-cephem-4-carboxylic acid (syn isomer) (3.6 g) in methylene chloride (7 ml) and anisole (3.6 ml) at ambient temperature and the mixture was stirred for 2 hours at the same temperature. To the resulting solution was added diisopropyl ether under stirring. The precipitates were collected by filtration and washed with diisopropyl ether. The precipitates were added to a mixture of ethyl acetate and water and the resultant mixture was adjusted to pH 7.5 with 20% aqueous solution of sodium carbonate. The separated aqueous layer was adjusted to pH 2.0 with 10% hydrochloric acid under ice-cooling. The resulting precipitates were collected by filtration, washed with ice-water and dried over phosphorus pentoxide in vacuo to give 7-[2-carboxymethoxyimino-2-(4-thiazolyl)acetamido]-3-tetrazolo[1,5-b]-pyridazin-6-yl)thiomethyl-3-cephem-4-carboxylic acid (syn isomer) (1.8 g).

IR (Nujol): 3200, 1775, 1715, 1675 cm$^{-1}$.

NMR (DMSO-d$_6$, δ): 3.75 (2H, q, J=16.0 Hz), 4.49 (2H, q, J=14.0 Hz), 4.74 (2H, s), 5.26 (1H, d, J=5.0 Hz), 5.96 (1H, dd, J=5.0 Hz, 8.0 Hz), 7.87 (1H, d, J=10.0 Hz), 8.10 (1H, d, J=2.0 Hz), 8.71 (1H, d, J=10.0 Hz), 9.31 (1H, d, J=2.0 Hz), 9.83 (1H, d, J=8.0 Hz).

EXAMPLE 5

The following compounds were obtained according to a similar manner to that of Example 4.

(1) 7-[2-Carboxymethoxyimino-2-(4-thiazolyl)acetamido]-3-(1-methyl-1H-tetrazol-5-yl)thiomethyl-3-cephem-4-carboxylic acid (syn isomer).

IR (Nujol): 1775, 1720, 1675 cm$^{-1}$.

NMR (DMSO-d$_6$, δ): 3.68 (2H, m), 3.91 (3H, s), 4.30 (2H, m), 4.65 (2H, s), 5.13 (1H, d, J=5.0 Hz), 5.82 (1H, dd, J=5.0 Hz, 8.0 Hz), 7.91 (1H, d, J=2.0 Hz), 9.11 (1H, d, J=2.0 Hz), 9.54 (1H, d, J=8.0 Hz).

(2) 7-[2-Carboxymethoxyimino-2-(4-thiazolyl)acetamido]-3-(5-methyl-1,3,4-thiadiazol-2-yl)thiomethyl-3-cephem-4-carboxylic acid (syn isomer).

IR (Nujol): 1775, 1720, 1675 cm$^{-1}$.

NMR (DMSO-d$_6$, δ): 2.66 (3H, s), 3.67 (2H, q, J=18.0 Hz), 4.36 (2H, q, J=14.0 Hz), 4.67 (2H, s), 5.16 (1H, d, J=5.0 Hz), 5.84 (1H, dd, J=5.0 Hz, 8.0 Hz), 7.90 (1H, d, J=2.0 Hz), 9.18 (1H, d, J=2.0 Hz), 9.53 (1H, d, J=8.0 Hz).

(3) 7-[2-Carboxymethoxyimino-2-(4-thiazolyl)acetamido]-3-(1H-1,2,3-triazol-5-yl)thiomethyl-3-cephem-4-carboxylic acid (syn isomer).

IR (Nujol): 1775, 1720, 1675 cm$^{-1}$.

NMR (DMSO-d$_6$, δ): 3.72 (2H, q, J=17.0 Hz), 4.03 (2H, q, J=14.0 Hz), 4.78 (2H, s), 5.26 (1H, d, J=5.0 Hz), 5.92 (1H, dd, J=5.0 Hz, 8.0 Hz), 8.05 (1H, s), 8.08 (1H, d, J=2.0 Hz), 9.27 (1H, d, J=2.0 Hz), 9.74 (1H, d, J=8 Hz).

(4) 7-[2-Carboxymethoxyimino-2-(4-thiazolyl)acetamido]-3-acetamidomethyl-3-cephem-4-carboxylic acid (syn isomer).

IR (Nujol): 3250, 1775, 1720, 1670, 1540 cm$^{-1}$.

NMR (DMSO-d$_6$, δ): 1.83 (3H, s), 3.47 (2H, ABq, J=18 Hz), 4.07 (2H, ABq, J=13 Hz), 4.67 (2H, s), 5.12 (1H, d, J=5 Hz), 5.82 (1H, dd, J=5 Hz, 8 Hz), 7.93 (1H, d, J=2 Hz), 8.05 (1H, t, J=6 Hz), 9.12 (1H, d, J=2 Hz), 9.50 (1H, d, J=8 Hz).

(5) 7-[2-Carboxymethoxyimino-2-(4-thiazolyl)acetamido]-3-(6-methylpyridazin-3-yl)thiomethyl-3-cephem-4-carboxylic acid (syn isomer)

IR (Nujol): 1770, 1675 cm$^{-1}$.

(6) 7-[2-Carboxymethoxyimino-2-(4-thiazolyl)acetamido]-3-mesylmethyl-3-cephem-4-carboxylic acid (syn isomer).

IR (Nujol): 3250, 1780, 1720, 1675, 1540 cm$^{-1}$.
IR (Nujol): 3250, 1780, 1720, 1675, 1540 cm$^{-1}$.

NMR (DMSO-d$_6$, δ): 3.02 (3H, s), 3.75 (2H, q, J=18 Hz), 4.50 (2H, ABq, J=13 Hz), 4.70 (2H, s), 5.30 (1H, d, J=5 Hz), 5.93 (1H, dd, J=5 Hz, 8 Hz), 8.00 (1H, d, J=2 Hz), 9.20 (1H, d, J=2 Hz), 9.65 (1H, d, J=8 Hz).

(7) 7-[2-Carboxymethoxyimino-2-(4-thiazolyl)acetamido]-3-(1,2,4-triazolo[4,3-b]pyridazin-6-yl)thiomethyl-3-cephem-4-carboxylic acid (syn isomer).

IR (Nujol): 1770, 1680 cm$^{-1}$.

EXAMPLE 6

The following compound was obtained by treating benzhydryl 7-[2-t-butoxycarbonylmethoxyimino-2-(4-thiazolyl)acetamido]-3-(6-methylpyridazin-3-yl)-thiomethyl-3-cephem-4-carboxylate (syn isomer) with trifluoroacetic acid and anisole according to a similar manner to that of Example 4.

7-[2-Carboxymethoxyimino-2-(4-thiazolyl)acetamido]-3-(6-methylpyridazin-3-yl)thiomethyl-3-cephem-4-carboxylic acid (syn isomer).

IR (Nujol): 1770, 1675 cm$^{-1}$.

NMR (DMSO-d$_6$, δ): 1.40–1.70 (3H, D$_2$O-overlap), 3.66 (2H, q, J=18.0 Hz), 4.16 (2H, m), 4.66 (2H, s), 5.16 (1H, d, J=5.0 Hz), 5.83 (1H, dd, J=5.0 Hz, 8.0 Hz), 7.38 (1H, d, J=9.0 Hz), 7.51 (1H, d, J=9.0 Hz), 7.94 (1H, s), 9.14 (1H, s), 9.58 (1H, d, J=8.0 Hz).

EXAMPLE 7

The following compound was obtained by treating benzhydryl 7-[2-t-butoxycarbonylmethoxyimino-2-(4-thiazolyl)acetamido]-3-(1,2,4-triazolo[4,3-b]pyridazin-6-yl)thiomethyl-3-cephem-4-carboxylate (syn isomer) with trifluoroacetic acid and anisole according to a similar manner to that of Example 4.

7-[2-Carboxymethoxyimino-2-(4-thiazolyl)acetamido]-3-(1,2,4-triazolo[4,3-b]pyridazin-6-yl)thiomethyl-3-cephem-4-carboxylic acid (syn isomer).

IR (Nujol): 1770, 1680 cm$^{-1}$.

NMR (DMSO-d$_6$, δ): 3.71 (2H, q, J=18.0 Hz), 4.08 (2H, q, J=14.0 Hz), 4.70 (2H, s), 5.20 (1H, d, J=4.0 Hz), 5.87 (1H, dd, J=4.0 Hz, 8.0 Hz), 7.28 (1H, d, J=10.0 Hz), 7.99 (1H, d, J=2.0 Hz), 8.23 (1H, d, J=10.0 Hz), 9.21 (1H, d, J=2.0 Hz), 9.41 (1H, s), 9.65 (1H, d, J=8.0 Hz).

EXAMPLE 8

Phosphorus trichloride (0.26 ml) was added to a solution of benzhydryl 7-[2-t-butoxycarbonylmethoxyimino-2-(4-thiazolyl)acetamido]-3-(1,2,4-triazolo[4,3-b]-pyridazin-6-yl)thiomethyl-3-cephem-4-carboxylate-1-oxide (syn isomer) (1.2 g) in N,N-dimethylformamide (10 ml) at −35° C. and the mixture was stirred for 35 minutes at −30° to −20° C. To a mixture of ethyl acetate and water was added the reaction mixture and the mixture was adjusted to pH 7.0 with 20% aqueous solution of sodium carbonate. The separated organic layer was washed with saturated aqueous solution of sodium chloride, dried over magnesium sulfate and evaporated to give benzhydryl 7-[2-t-butoxycarbonylmethoxyimino-2-(4-thiazolyl)-acetamido]-3-(1,2,4-triazolo[4,3-b]pyridazin-6-yl)-thiomethyl-3-cephem-4-carboxylate (syn isomer) (1.0 g).

IR (Nujol): 1775, 1715, 1675 cm$^{-1}$.

NMR (DMSO-d$_6$, δ): 1.43 (9H, s), 3.75 (2H, q, J=18.0 Hz), 4.14 (2H, m), 4.68 (2H, s), 5.25 (1H, d, J=4.0 Hz), 5.95 (1H, dd, J=4.0 Hz, 8.0 Hz), 7.60–7.68 (11H, m), 7.95 (1H, d, J=2.0 Hz), 8.16 (1H, d, J=10.0 Hz), 9.06 (1H, d, J=2.0 Hz), 9.21 (1H, s), 9.65 (1H, d, J=8.0 Hz).

EXAMPLE 9

Phosphorus trichloride (1.5 g) was added to a solution of 7-[2-t-butoxycarbonylmethoxyimino-2-(4-thiazolyl)acetamido]-3-mesylmethyl-3-cephem-4-carboxylic acid-1-oxide (syn isomer (2.1 g) in N,N-dimethylformamide (20 ml) at −50° C. and the solution was stirred at −40° to −30° C. for 10 minutes. The reaction mixture was poured into a mixture of cold water (200 ml) and ethyl acetate (150 ml). The separated organic layer was washed with water (50 ml), dried over magnesium sulfate and evaporated to give 7-[2-t-butoxycarbonylmethoxyimino-2-(4-thiazolyl)acetamido]-3-mesylmethyl-3-cephem-4-carboxylic acid (syn isomer) (0.9 g).

IR (Nujol): 3250, 1770, 1710, 1650, 1550 cm$^{-1}$

NMR (DMSO-d$_6$, δ): 1.45 (9H, s), 3.0 (3H, s), 3.73 (2H, broad s), 4.50 (2H, ABq, J=13 Hz), 4.67 (2H, s), 5.30 (1H, d, J=5 Hz), 5.90 (1H, dd, J=5 Hz, 8 Hz), 7.97 (1H, d, J=2 Hz), 9.20 (1H, d, J=2 Hz), 9.67 (1H, d, J=8 Hz).

EXAMPLE 10

The following compounds were obtained according to similar manners to those of Example 8 and 9.

(1) 7-[2-t-Butoxycarbonylmethoxyimino-2-(4-thiazolyl)-acetamido]-3-(tetrazolo[1,5-b]pyridazin-6-yl)-thiomethyl-3-cephem-4-carboxylic acid (syn isomer).

IR (Nujol): 1770, 1710, 1670 cm$^{-1}$.

(2) 7-[2-Carboxymethoxyimino-2-(4-thiazolyl)acetamido]-3-(tetrazolo[1,5-b]pyridazin-6-yl)thiomethyl-3-cephem-4-carboxylic acid (syn isomer).

IR (Nujol): 3200, 1775, 1715, 1675 cm$^{-1}$.

(3) 7-[2-t-Butoxycarbonylmethoxyimino-2-(4-thiazolyl)-acetamido]-3-(1-methyl-1H-tetrazol-5-yl)thiomethyl-3-cephem-4-carboxylic acid (syn isomer).

IR (Nujol): 3260, 1760, 1720, 1680, 1630 cm$^{-1}$.

(4) 7-[2-Carboxymethoxyimino-2-(4-thiazolyl)acetamido]-3-(1-methyl-1H-tetrazol-5-yl)thiomethyl-3-cephem-4-carboxylic acid (syn isomer)

IR (Nujol): 1775, 1720, 1675 cm$^{-1}$.

(5) 7-[2-t-Butoxycarbonylmethoxyimino-2-(4-thiazolyl)-acetamido]-3-(5-methyl-1,3,4-thiadiazol-2-yl)-thiomethyl-3-cephem-4-carboxylic acid (syn isomer).

IR (Nujol): 1770, 1720, 1670 cm$^{-1}$.

(6) 7-[2-Carboxymethoxyimino-2-(4-thiazolyl)acetamido]-3-(5-methyl-1,3,4-thiadiazol-2-yl)thiomethyl-3-cephem-4-carboxylic acid (syn isomer).

IR (Nujol): 1775, 1720, 1675 cm$^{-1}$.

(7) 7-[2-t-Butoxycarbonylmethoxyimino-2-(4-thiazolyl)acetamido]-3-(1H-1,2,3-triazol-5-yl)thiomethyl-3-cephem-4-carboxylic acid (syn isomer).

IR (Nujol): 1770, 1710, 1670 cm$^{-1}$.

(8) 7-[2-Carboxymethoxyimino-2-(4-thiazolyl)acetamido]-3-(1H-1,2,3-triazol-5-yl)thiomethyl-3-cephem-4-carboxylic acid (syn isomer).

IR (Nujol): 1775, 1720, 1675 cm$^{-1}$.

(9) 7-[2-t-Butoxycarbonylmethoxyimino-2-(4-thiazolyl)-acetamido]-3-acetamidomethyl-3-cephem-4-carboxylic acid (syn isomer).

IR (Nujol): 3250, 1780, 1710, 1680, 1600, 1550 cm$^{-1}$.

(10) 7-[2-Carboxymethoxyimino-2-(4-thiazolyl)acetamido]-3-acetamidomethyl-3-cephem-4-carboxylic acid (syn isomer).

IR (Nujol): 3250, 1775, 1720, 1670, 1540 cm$^{-1}$.

(11) Benzhydryl 7-[2-t-butoxycarbonylmethoxyimino-2-(4-thiazolyl)acetamido]-3-(6-methylpyridazin-3-yl)-thiomethyl-3-cephem-4-carboxylate (syn isomer).

IR (Nujol): 1780, 1720, 1675, 1630 cm$^{-1}$.

NMR (DMSO-d$_6$, δ): 1.45 (9H, s), 2.32 (3H, s), 3.73 (2H, m), 4.20 (2H, m), 4.67 (2H, s), 5.28 (1H, d, J=5.0 Hz), 5.98 (1H, dd, J=5.0 Hz, 8.0 Hz), 7.00 (1H, s), 7.17–7.73 (12H, m), 7.98 (1H, d, J=2.0 Hz), 9.21 (1H, d, J=2.0 Hz), 9.67 (1H, d, J=8.0 Hz).

(12) 7-[2-Carboxymethoxyimino-2-(4-thiazolyl)acetamido]-3-(6-methylpyridazin-3-yl)thiomethyl-3-cephem-4-carboxylic acid (syn isomer).

IR (Nujol): 1770, 1675 cm$^{-1}$.

(13) 7-[2-Carboxymethoxyimino-2-(4-thiazolyl)acetamido]-3-mesylmethyl-3-cephem-4-carboxylic acid (syn isomer).

IR (Nujol): 3250, 1780, 1720, 1675, 1540 cm$^{-1}$.

(14) 7-[2-Carboxymethoxyimino-2-(4-thiazolyl)acetamido]-3-(1,2,4-triazolo[4,3-b]pyridazin-6-yl)thiomethyl-3-cephem-4-carboxylic acid (syn isomer).

IR (Nujol): 1770, 1680 cm$^{-1}$.

EXAMPLE 11

6-Mercapto-1,2,4-triazolo[4,3-b]pyridazine (4.7 g) was added to a stirred suspension of benzhydryl 7-[2-t-butoxycarbonylmethoxyimino-2-(4-thiazolyl)acetamido]-3-chloromethyl-3-cephem-4-carboxylate (syn isomer) (5.0 g) and sodium iodide (4.6 g) in N,N-dimethylformamide (35 ml) and the mixture was stirred for 2 hours at ambient temperature. To the reaction mixture was added a mixture of ethyl acetate and water and then the resultant mixture was adjusted to pH 7.5 with 20% aqueous solution of sodium carbonate. The separated organic layer was washed with saturated aqueous solution of sodium chloride and dried over magnesium sulfate. The crude product obtained by concentration of organic layer was purified by silica gel column chromatography using ethyl acetate as an eluate. The fractions containing the object compound were evaporated to give benzhydryl 7-[2-t-butoxycarbonylmethoxyimino-2-(4-thiazolyl)acetamido]-3-(1,2,4-triazolo[4,3-b]pyridazin-6-yl)thiomethyl-3-cephem-4-carboxylate (syn isomer) (1.2 g).

IR (Nujol): 1775, 1715, 1675 cm$^{-1}$.

NMR (DMSO-d$_6$, δ): 1.43 (9H, s), 3.75 (2H, q, J=18.0 Hz), 4.14 (2H, m), 4.68 (2H, s), 5.25 (1H, d, J=4.0 Hz), 5.95 (1H, dd, J=4.0 Hz, 8.0 Hz), 7.60–7.68 (11H, m), 7.95 (1H, d, J=2.0 Hz), 8.16 (1H, d, J=10.0 Hz), 9.06 (1H, d, J=2.0 Hz), 9.21 (1H, s), 9.65 (1H, d, J=8.0 Hz).

EXAMPLE 12

The following compounds were obtained according to a similar manner to that of Example 11.

(1) 7-[2-t-Butoxycarbonylmethoxyimino-2-(4-thiazolyl)-acetamido]-3-(tetrazolo[1,5-b]pyridazin-6-yl)thiomethyl-3-cephem-4-carboxylic acid (syn isomer).

IR (Nujol): 1770, 1710, 1670 cm$^{-1}$.

(2) 7-[2-Carboxymethoxyimino-2-(4-thiazolyl)acetamido]-3-(tetrazolo[1,5-b]pyridazin-6-yl)thiomethyl-3-cephem-4-carboxylic acid (syn isomer).

IR (Nujol): 3200, 1775, 1715, 1675 cm$^{-1}$.

(3) 7-[2-t-Butoxycarbonylmethoxyimino-2-(4-thiazolyl)-acetamido]-3-(1-methyl-1H-tetrazol-5-yl)thiomethyl-3-cephem-4-carboxylic acid (syn isomer).

IR (Nujol): 3260, 1760, 1720, 1680, 1630 cm$^{-1}$.

(4) 7-[2-Carboxymethoxyimino-2-(4-thiazolyl)acetamido]-3-(1-methyl-1H-tetrazol-5-yl)thiomethyl-3-cephem-4-carboxylic acid (syn isomer).

IR (Nujol): 1775, 1720, 1675 cm$^{-1}$.

(5) 7-[2-t-Butoxycarbonylmethoxyimino-2-(4-thiazolyl)-acetamido]-3-(5-methyl-1,3,4-thiadiazol-2-yl)-thiomethyl-3-cephem-4-carboxylic acid (syn isomer).

IR (Nujol): 1770, 1720, 1670 cm$^{-1}$.

(6) 7-[2-Carboxymethoxyimino-2-(4-thiazolyl)acetamido]-3-(5-methyl-1,3,4-thiadiazol-2-yl)thiomethyl-3-cephem-4-carboxylic acid (syn isomer).

IR (Nujol): 1775, 1720, 1675 cm$^{-1}$.

(7) 7-[2-t-Butoxycarbonylmethoxyimino-2-(4-thiazolyl)-acetamido]-3-(1H-1,2,3-triazol-5-yl)thiomethyl-3-cephem-4-carboxylic acid (syn isomer).

IR (Nujol): 1770, 1710, 1670 cm$^{-1}$.

(8) 7-[2-Carboxymethoxyimino-2-(4-thiazolyl)acetamido]-3-(1H-1,2,3-triazol-5-yl)thiomethyl-3-cephem-4-carboxylic acid (syn isomer).

IR (Nujol): 1775, 1720, 1675 cm$^{-1}$.

(9) Benzhydryl 7-[2-t-butoxycarbonylmethoxyimino-2-(4-thiazolyl)acetamido]-3-(6-methylpyridazin-3-yl)-thiomethyl-3-cephem-4-carboxylate (syn isomer).

IR (Nujol): 1780, 1720, 1675, 1630 cm$^{-1}$.

(10) 7-[2-Carboxymethoxyimino-2-(4-thiazolyl)acetamido]-3-(6-methylpyridazin-3-yl)thiomethyl-3-cephem-4-carboxylic acid (syn isomer).

IR (Nujol): 1770, 1675 cm$^{-1}$.

(11) 7-[2-Carboxymethoxyimino-2-(4-thiazolyl)acetamido]-3-(1,2,4-triazolo[4,3-b]pyridazin-6-yl)thiomethyl-3-cephem-4-carboxylic acid (syn isomer).

IR (Nujol): 1770, 1680 cm$^{-1}$.

What we claim is:

1. A compound of the formula:

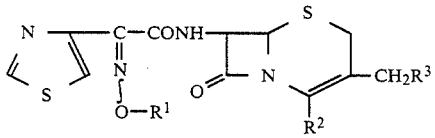

wherein $R^1$ is carboxy $(C_1-C_6)$ alkyl or esterified carboxy $(C_1-C_6)$ alkyl, $R^2$ is carboxy or an esterified carboxy group, and $R^3$ is $(C_1-C_6)$ alkanoylamino, $(C_1-C_6)$ alkanesulfonyl, triazolylthio, tetrazolylthio having $(C_1-C_6)$ alkyl, pyridazinylthio having $(C_1-C_6)$ alkyl, thiadiazolylthio having $(C_1-C_6)$ alkyl, triazolopyridazinylthio or tetrazolopyridazinylthio, and pharmaceutically acceptable salts thereof.

2. Syn isomer of claim 1.

3. A compound of claim 2, wherein $R^1$ is carboxy$(C_1-C_6)$alkyl or $(C_1-C_6)$ alkoxycarbonyl-$(C_1-C_6)$alkyl, $R^2$ is carboxy, and $R^3$ is $(C_1-C_6)$ alkanoylamino.

4. A compound of claim 3, which is 7-[2-carboxymethoxyimino-2-(4-thiazolyl)acetamido]-3-acetamidomethyl-3-cephem-4-carboxylic acid (syn isomer).

5. A compound of claim 2, wherein $R^1$ is carboxy$(C_1-C_6)$alkyl or lower alkoxycarbonyl-$(C_1-C_6)$alkyl, $R^2$ is carboxy, and $R^3$ is $(C_1-C_6)$ alkanesulfonyl.

6. A compound of claim 5, which is 7-[2-carboxymethoxyimino-2-(4-thiazolyl)acetamido]-3-mesylmethyl-3-cephem-4-carboxylic acid (syn isomer).

7. A compound of claim 2, wherein $R^1$ is carboxy$(C_1-C_6)$alkyl or $(C_1-C_6)$ alkoxycarbonyl-$(C_1-C_6)$alkyl, $R^2$ is carboxy or diphenyl(lower)alkoxycarbonyl, and $R^3$ is triazolylthio, tetrazolylthio having $(C_1-C_6)$alkyl, pyridazinylthio having $(C_1-C_6)$ alkyl, thiadiazolylthio having $(C_1-C_6)$ alkyl, triazolopyridazinylthio or tetrazolopyridazinylthio.

8. A compound of claim 7, which is 7-[2-carboxymethoxyimino-2-(4-thiazolyl)acetamido]-3-(tetrazolo[1,5-b]pyridazin-6-yl)thiomethyl-3-cephem-4-carboxylic acid (syn isomer).

9. An antibacterial composition comprising an effective amount of a compound of claim 1 in association with a pharmaceutically acceptable substantially nontoxic carrier or excipient.

10. A compound of the formula:

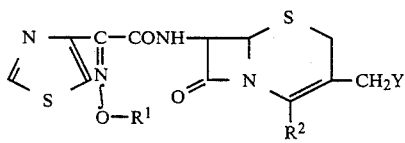

wherein $R^1$ is carboxy$(C_1-C_6)$alkyl or esterified carboxy$(C_1-C_6)$alkyl, $R^2$ is carboxy or an esterified carboxy group, and Y is halogen or a salt thereof.

* * * * *